United States Patent
Smith

(10) Patent No.: US 9,562,095 B2
(45) Date of Patent: Feb. 7, 2017

(54) METHOD FOR TREATING TUMORS THAT POSSESS THE CCK-C RECEPTOR WITH THE 3B9.1 MONOCLONAL ANTIBODY

(71) Applicant: Jill P. Smith, Camp Hill, PA (US)

(72) Inventor: Jill P. Smith, Camp Hill, PA (US)

( * ) Notice: Subject to any disclaimer, the term of this patent is extended or adjusted under 35 U.S.C. 154(b) by 0 days.

(21) Appl. No.: 14/474,284

(22) Filed: Sep. 1, 2014

(65) Prior Publication Data
US 2016/0168246 A1   Jun. 16, 2016

Related U.S. Application Data

(63) Continuation-in-part of application No. 12/772,758, filed on May 3, 2010, now Pat. No. 8,821,872.

(51) Int. Cl.
| | |
|---|---|
| *C07K 16/28* | (2006.01) |
| *A61K 39/395* | (2006.01) |
| *C07K 16/30* | (2006.01) |
| *A61K 45/06* | (2006.01) |
| *G01N 33/574* | (2006.01) |

(52) U.S. Cl.
CPC ......... *C07K 16/28* (2013.01); *A61K 39/3955* (2013.01); *A61K 45/06* (2013.01); *C07K 16/2869* (2013.01); *C07K 16/303* (2013.01); *G01N 33/57438* (2013.01); *G01N 33/57446* (2013.01); *C07K 2317/11* (2013.01); *C07K 2317/33* (2013.01); *C07K 2317/34* (2013.01); *G01N 2333/72* (2013.01)

(58) Field of Classification Search
None
See application file for complete search history.

(56) References Cited

PUBLICATIONS

Patrick Chames, Marc Van Regenmortel, Etienne Weiss, Daniel Baty. Therapeutic antibodies: successes, limitations and hopes for the future. Br J Pharmacol. May 2009; 157(2) DOI: 10.1111/j.1476-5381.2009.00190.x.
Ann Richmond, Yingjun. Mouse xenograft models vs GEM models for human cancer therapeutics. Dis Model Mech. Sep.-Oct. 2008; 1(2-3): 78-82. DOI: 10.1242/dmm.000976.
J-R Azanza, B Sadaba, A Gomez-Guiu. Monoclonal antibodies: Pharmacokinetics as a basis for new dosage regimens? J Oncol Pharm Practice, 2015, vol. 21(5) 370-376. DOI: 10.1177/1078155214538085.
Daniel R. Getts, Meghann T. Getts, Derrick P. McCarthy, Emily ML Chastain, Stephen D. Miller. Have we overestimated the benefit of human(ized) antibodies? mAbs. vol. 2. 2010. DOI.10.4161/mabs.2.6.13601.

*Primary Examiner* — Elly-Gerald Stoica
(74) *Attorney, Agent, or Firm* — Laurence Weinberger

(57) ABSTRACT

Human pancreatic cancer cells possess a distinct plasma membrane CCK receptor variant that can be differentiated from the classic CCK-B receptor with selective monoclonal antibodies. Use of this receptor may be helpful in early detection or treatment of patients with pancreatic cancer.

2 Claims, 5 Drawing Sheets

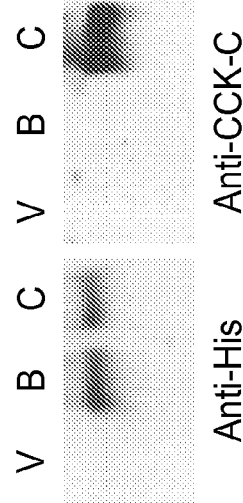
FIG.1
FIG.2
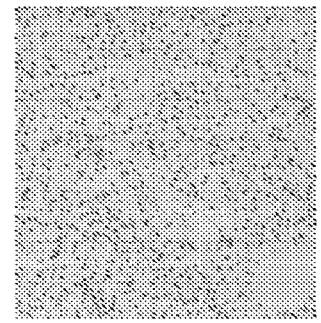
FIG.3
FIG.4A  FIG.4B  FIG.4C  FIG.4D

METHOD FOR TREATING TUMORS THAT POSSESS THE CCK-C RECEPTOR WITH THE 3B9.1 MONOCLONAL ANTIBODY

Benefit of U.S. Provisional Application No. 61/174,647 is hereby claimed. The work on which this patent application is based was supported by NIH #R01 CA117926 and ACS #PF-04-104-01-CSM. This application is a continuation-in-part of U.S. application Ser. No. 12/772,758 filed on May 3, 2010, benefit of which is also claimed.

BACKGROUND

Gastrin stimulates growth of human pancreatic cancer through a splice variant of the CCK-B receptor called the CCK-C receptor. This receptor retains the 4th intron which is transcribed and translated in human cancer but not in mice or normal human tissue.

HYPOTHESIS

It is hypothesized that the CCK-C receptor is unique and can be differentiated from the standard CCK-B receptor by targeting the unspliced section in imaging and RNA assays.

METHODS

Monoclonal antibodies were raised to the CCK-C receptor in BALB/c mice using a KLH-conjugated 20-mer peptide from the 5' end of the 4th intron of the CCK-B receptor. After boosting, the spleen and lymph nodes were harvested and a single-cell suspension of lymphocytes prepared. The lymphocytes were then fused with P3X63-Ag8.653 nonsecreting mouse myeloma fusion partner cells and screened by ELISA assay using unconjugated immunizing peptide. Monoclonal antibodies were affinity purified, isotyped and assessed using His epitope-tagged CCK-C and CCK-B receptor positive controls. Verified monoclonal antibodies were used to determine localization of the CCK-C receptor using confocal microscopy. In parallel, over-expressing cancer lines and a panel of wild-type human pancreatic cancer lines were evaluated by RT-PCR. Over-expressing human cancer cells were developed by transfecting BxPC-3 and MIA PaCa2 pancreatic cancer cells with pcDNA3.1+ CCK-C cDNA construct including the normally-spliced introns 2 and 3 in order to differentiate receptor mRNA from genomic and transfected DNA sequences.

RESULTS

Two monoclonal antibodies, 3B9 and 28H8, exhibited both specificity and selectivity to the CCK-C receptor. No cross-reactivity occurred to the CCK-B receptor. Isotyping of the monoclonal antibodies revealed both to be isotype IgG1 antibodies. Immunocytochemistry showed CCK-C reactivity associated with the plasma membrane and cytoplasm of pancreatic cancer cells. RT-PCR detected CCK-C receptor mRNA in 67% of wild type human pancreatic cancer cell lines. The monoclonal 3B9.1 Ab was found to inhibit tumor growth in SCID mice bearing established human cancer xenografts and to prolong survival.

CONCLUSION

Some human cancer cells possess a distinct plasma membrane CCK receptor variant that can be differentiated from the classic CCK-B receptor with selective monoclonal antibodies. Use of the 3B9.1 monoclonal Ab to the CCK-C receptor may be helpful in early detection and treatment of patients with cancers possessing the CCK-C receptor.

BRIEF DESCRIPTION OF THE FIGURES

FIG. 1 is an ELISA assay screening of media from clones of hybridomas for reactivity against the CCK-C peptide. Several positive antibody producing clones were identified.

FIG. 2 illustrates an Immunocytochemical reaction to human pancreatic cancer cells in culture with a monoclonal (murine) antibody to the human CCK-C receptor. Secondary antibody is a rhodamine-labeled goat-anti mouse antibody.

FIG. 3 illustrates that newly developed monoclonal antibodies are specific to the CCK-C receptor. HEK-293 cells were transiently transfected with pcDNA3.1 (vector-only, V) or 6×His epitope-tagged receptor cDNA (CCK-B, B; CCK-C, C).

FIG. 4 (consisting of FIG. 4A, FIG. 4B, FIG. 4C, and FIG. 4D) below shows immunoreactivity in the cancer cells of the pancreas but not in normal tissue from the same subject nor in the surrounding fibrous connective tissue. FIG. 4A: H&E Cancer; FIG. 4B: CCK-C antibody in pancreatic cancer; FIG. 4C: Cancer non-immune antibody control; FIG. 4D: Normal pancreas, negative.

INTRODUCTION

Figure 5:
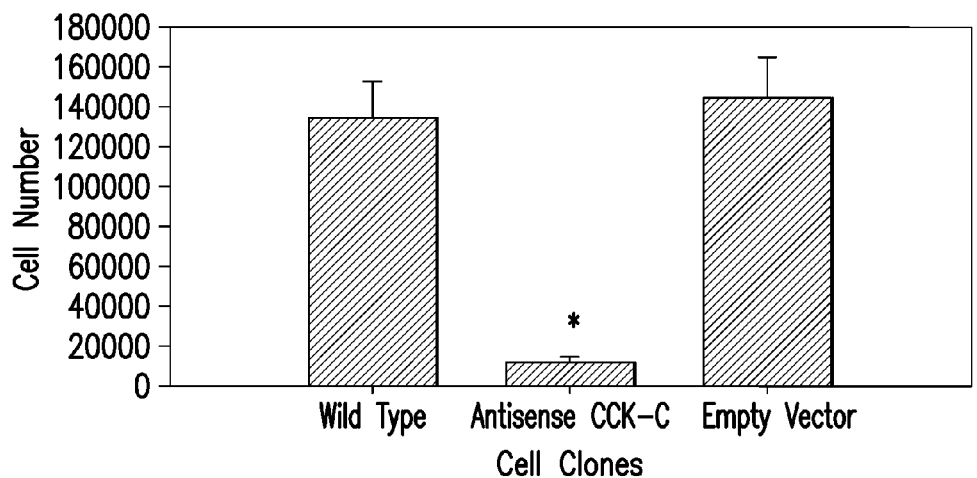
FIG. 5 illustrates the growth of BxPC-3 cells in vitro in serum-free medium over 6 days. Wild type and empty vector transfected BxPC-3 cells increased nearly 6-fold over the number plated. BxPC-3 cells transfected with the antisense cDNA to the CCK-C receptor failed to increase in growth over 6 days and were significantly less in number compared to wild type and empty vector transfected cells. *Significantly different from wild type and empty vector transfected cells at $p<0.005$.

Natural History and Treatment of Pancreatic Cancer

Pancreatic cancer is a fatal malignancy estimated to occur in approximately 37,680 Americans in 2009 and ranks as the fourth most common cause of cancer-related mortality in the United States.[1] With a five-year survival rate of less than 1%, pancreatic cancer remains the lowest of all malignancies, and median survival is three to six months with only 10% of patients surviving two years.[2] Surgical resection of the tumor improves median survival to 17-20 months, but five-year survival is still less than 10%.[3]

Pancreatic cancer is most commonly diagnosed in advanced stages, and therefore, chemotherapy remains the major treatment modality for this disease. Among the chemotherapeutic agents tested, gemcitabine has been used the most either alone or in combination with other agents.[4-6] Although various combinations of other drugs with gemcitabine$_4$ or with concurrent radiation[7] appear to improve the response rates, a clear survival benefit has not yet been demonstrated. Because of the overall poor response of pancreatic cancer to chemotherapy and its toxicity, researchers have been targeting treatment regimes toward the genetic alterations and peptide growth factors involved with proliferation of pancreatic cancer cells[8]. Trastuzumab (Herceptin) is a humanized monoclonal antibody against the HER-2/neu receptor and has shown significant clinical activity against metastatic breast cancer[9]. Recent attention has been directed at EGF inhibition using an EGF monoclonal antibody, cetuximab with gemcitabine[10] for the treatment of pancreatic cancer. Unfortunately the median time to progression in this Phase 2 study was 3.8 months and overall median survival was 7.1 months[10]. Because of recent promising results in colon cancer using an angiogenesis inhibitor, bevacizumab,[11] this therapy was also tried in subjects with pancreatic cancer with some promising results[12].

Role of Gastrin and CCK Physiologically and on Cancers:

The gastrointestinal peptides cholecystokinin (CCK) and gastrin are involved physiologically in secretion of gastric acid[13] and pancreatic juices[14], satiety[15], and growth of the gastrointestinal tract[16]. Gastrin is an important growth factor for the developing[17] and adult[18] digestive system, and has been reported to be trophic for the entire gastrointestinal tract[19]. In addition to their role in regulation of growth of the normal gastrointestinal tract, gastrin and CCK have been shown to play a role in several neoplasias, including colon cancer[20-23], gastrin cancer[24,25], and lung cancer[26]. Our research investigations have previously shown that human pancreatic cancer cells grown in culture[27] or as xenografted tumors to athymic nude mice[28] are stimulated to grow by the gastrointestinal peptides CCK and gastrin[29]. Other investigators have confirmed that exogenous administration of CCK stimulates growth of carcinogen-induced pancreatic cancer in animal models[30,31].

During development, gastrin immunoreactivity is found in the fetal pancreas, but its expression is not detected after birth[32]. In the adult, the only gastrin immunoreactivity is found in the G-cells of the gastric antrum[32]. Recently, gastrin immunoreactivity has been identified in human pancreatic cancer cells and tissues[29,33], suggesting the re-expression of this peptide in the malignant state. Treatment of pancreatic cancer cells in vitro with antisense oligonucleotides to gastrin decreased cell proliferation, suggesting that growth of this human malignancy may occur through an autocrine mechanism[33].

Cholecystokinin Receptors (Normal and in Cancer):

Three types of CCK receptors have been identified[34-37]: CCK-A (or CCK$_1$), the CCK-B (or CCK$_2$), and the CCK-C receptor[38]. Receptor binding studies[39,40] suggested that the receptor associated with pancreatic cancer more closely resembles a CCK-B receptor rather than a CCK-A receptor. Although some characteristics of this cancer-associated receptor were unique from the classic CCK-B recepto[41] including: i.) its greater affinity toward gastrin than CCK[40], ii.) the inability to impair cell growth with physiologic doses of the CCK-B receptor antagonist[33], and iii.) the lack of an intracellular calcium second messenger response to gastrin or CCK in fura-2 loaded pancreatic cancer cells[42]. Recently the CCK receptor of pancreatic cancer cells has been cloned, sequenced and characterized[38,43] and is a splice variant of the CCK-B receptor. In addition to the physiologic differences compared to the CCK-B receptor, the splice variant of the CCK-B receptor retains intron 4 that codes for an additional 69 amino acids which changes the structure of the receptor protein. Because this cancer receptor is found in neoplastic cells and not found in normal pancreatic tissues, has unique properties from the CCK-B receptor, and is the third CCK receptor of the family, it has been termed the "CCK-C" receptor[38].

Investigators have identified other splice variants of the CCK-B receptor[44,45] and have termed these the short and long CCK-B isoforms depending on the presence or deletion (short) of 5 amino acids. Recently, Hellmich and colleagues[46] have identified the CCK-C receptor with the fully expressed 4th intron in human colon cancers. Ding and coworkers[47] found that pancreatic cancer cells express the CCK-C receptor as a result of reduced activity of U2AF35 nuclear ribonucleoprotein particle splicing factor.

Evidence that Gastrin Mediates its Growth Effects Through a CCK Receptor in Cancer:

Although previous in vitro and in vivo studies showed an influence of gastrin on growth of pancreatic cancer cells, and radioligand binding studies demonstrated a physiologic receptor, the relationship between gastrin and the CCK-C receptor with respect to growth had been circumstantial. For example, gastrin could actually be mediating its proliferative effects in a nonreceptor-mediated fashion. A strategy was devised to investigate whether both gastrin and its receptor are required for growth activity, and if there is a necessary interaction between these two proteins to perform this function. In an experimental model where gastrin expression and translation was eliminated through antisense transfection[48], growth of human pancreatic cancer cells was slowed compared to wild type or empty vector transfected cells. Although growth was impaired, cells continued to proliferate, suggesting that perhaps other growth factors were involved, ie, CCK. However, when the CCK-C receptor expression and translation were attenuated by antisense transfection experiments, human pancreatic cancer cells failed to replicate[49]. These studies and others[29,33,38,48,50,51] indicate that growth of human pancreatic cancer appears to be controlled by the tonic activity of gastrin acting at a CCK receptor. Moreover, one could postulate that the increased production of peptide and/or receptor may be involved in the pathogenesis of pancreatic cancer. Disruption of this pathway through the blockade of mRNA transcription or translation, or the interference with the interaction between gastrin and the CCK-C receptor, may prove to be a fruitful area of development for treatment of patients with pancreatic cancer. It is hypothesized that the CCK-C receptor is unique and can be differentiated from the standard CCK-B receptor by targeting the unspliced section which may prove to be useful in the future for early detection or treatment of pancreatic cancer.

Figure 9:
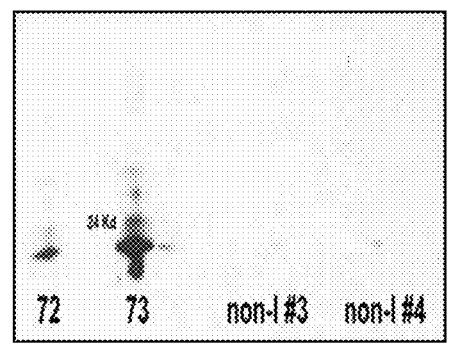
FIG. 9 is a Western Analysis of a CCK-C GST-Fusion Peptide indicating a greater binding to peptide with CCK-C 3B9.1 Ab (#73) than #72 and that no binding was detected with the non-immune Abs.
Figure 10:
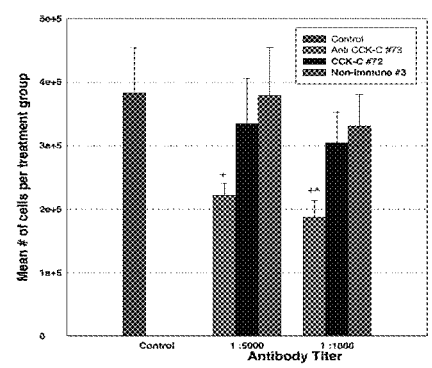
FIG. 10 shows the results of a growth study indicating that CCK-C 3B9.1 Ab (#73) decreases cell number by 41.5% to 51.2% at Ab titers 1:5000 or 1:1000 respectively. No growth inhibition was detected in cells treated with CCK-C Ab #72—significantly different non-immune and control at $p<0.05$.
Figure 11:
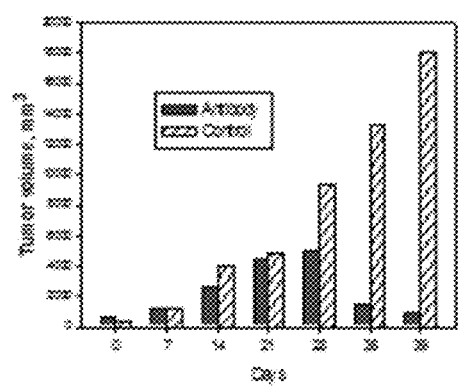
FIG. 11 shows that tumor volumes were significantly reduced in SCID immunodeficient mice bearing human pancreatic cancer xenografts that were treated with the monoclonal 3B9.1 antibody to the CCK-C receptor compared to animals treated with diluent.

Evidence that Immunotherapy to the Epitope on the Splice Variant Receptor Inhibits Growth Since the epitope appeared to be in the $3^{rd}$ intracellular loop and not readily exposed to the extracellular domain, it was critical that we demonstrate the antibody was capable of interacting with the receptor during cell division and receptor recycling by impairing growth. In the next series of experiments we tested different antibodies isolated from our mice based upon binding affinity to protein in Western analysis. (FIG. 9) shows that the monoclonal antibody 3B9.1 (#73) had the highest binding affinity. The monoclonal 3B9.1 Ab was then tested to determine its affect on cell proliferation. The effect of antibody treatment with 3B9.1 (#73) on cancer cell growth in vitro significantly inhibited cell growth in a dose related fashion (i.e., Titers of 1:1000 inhibited growth more than 1:5000) (FIG. 10). In an animal model using SCID mice bearing established human pancreatic cancer xenografts (900 mm$^3$), mice that were treated daily for 39 days with 0.1 ml of the 389.1 monoclonal antibody intratumorally had significant regression in tumor size and prolonged survival compared to control mice treated with intratumoral diluent (FIG. 11). The experiment was stopped by the veterinarians due to the large size of tumors in the control animal group. This clearly demonstrates that the monoclonal 3B9.1 Ab may be used to treat human tumors and to prolong survival of patients with tumors that posses the CCK-C receptor.

Methods:

Development of CCK-C Receptor Antibodies

A 12-amino acid peptide from the unique portion of the unspliced 4th intron of the CCK-C receptor (distinct from the known CCK-A and CCK-B receptors) was conjugated with KLH and mixed in Freud's adjuvant, to increase immunogenicity. Antisera to the CCK-C peptide was generated in Leghorn chickens by Cocalico Biologics, Inc (Reamstown, Pa.) Pior to immunization, preimmune serum and eggs were collected. After inoculation, the chickens were boosted every 3 weeks and serum analyzed for immunoreactivity. The eggs were harvested and antibody extracted from yolks of immunoreactive chickens. Description of this polyclonal antibody and its use in recognizing the CCK-C receptor in human cancer cells and extracts by Western analysis has been published[38,43,52]

Using a 20-amino acid peptide from the similar area of the unspliced 4th intron of the CCK-C receptor of pancreatic cancer cells conjugated with KLH and mixed in Freud's adjuvant, to increase immunogenicity, we raised mouse antibodies to the receptor in BALB/c mice. In addition and for control purposes, we also raised murine antibodies against the human CCK-B receptor. After several months of boosting, the spleen and lymph nodes were harvested and a single-cell suspension of lymphocytes prepared. The suspensions were then fused with P3X63-Ag8.653 nonsecreting mouse myeloma fusion partner cells at a 1:1 ratio and plated into 96-well plates. Positive clones were identified by and ELISA assay using CCK-C receptor peptide as the ligand (FIG. 1). In addition and for control purposes, murine antibodies were also raised against the human CCK-B receptor. After several months of boosting, the spleen and lymph nodes were harvested and a single-cell suspension of lymphocytes prepared. The suspensions were then fused with P3X63-Ag8.653 nonsecreting mouse myeloma fusion partner cells at a 1:1 ratio and plated into 96-well plates. Positive clones were identified by and ELISA assay using CCK-C receptor peptide as the ligand. Monoclonal antibodies were affinity purified using a Pierce Sulfolink column from (ThermoFisher, Rockford, Ill.) and isotyped with a kit from Biomeda, Foster City, Calif. (FIG. 2).

Specificity of the CCK-C Receptor by Western Analysis

HEK-293 cells were transiently transfected with pcDNA3.1 (vector-only) or pcDNA3.1 containing 6xHis epitope-tagged receptor cDNA for the CCK-B or CCK-C receptors. Cells were harvested and 80 µg of protein homogenates were loaded onto a 10% Tris-HCl (10% resolving gel/4% stacking gel) gel for polyacrylamide electrophoresis. Gel electrophoresis was run at 1× running buffer (Sigma, St. Louis, Mo.), 10 g SDS (Sigma) 144 g glycine (Fisher, Fairlawn, N.J.), and transferred to nitrocellulose (Scleicher & Schuell, Keene, N.H.) with Towbin's transfer buffer (25 nM Tris, 192 mM glycine). Blots were prehybridized in Tris buffer for 2 hrs at pH 7.4 containing 5% milk then overnight in Tris buffer at 4° C. containing either the CCK-B or the CCK-C murine antibodies to evaluate specificity (FIG. 3).

Overexpression of the CCK-C Receptor in Pancreatic Cancer Cells:

Over-expressing human cancer cells were developed by transfecting BxPC-3 and MIA PaCa2 pancreatic cancer cells with pcDNA3.1+ CCK-C cDNA construct including the normally-spliced introns 2 and 3 in order to differentiate receptor mRNA from genomic and transfected DNA sequences. Control cells were transfected with empty vector. Log phase cells were transfected with Lipofectamine-2000 (Invitrogen, Carlsbad, Calif.). Positive clones were selected by G418 resistance and tested for receptor expression by RT-PCR. FIG. 4 shows immunoreactivity in the cancer cells of the pancreas but not in normal tissue from the same subject nor in the surrounding fibrous connective tissue. The above knock-out experiments are important because they demonstrate that the CCK-C receptor found in pancreatic cancer cells is functional and directly related to cancer cell growth. Since the receptor is functionally significant, it may be a unique target for early detection or therapy (FIG. 5).

Figure 6:
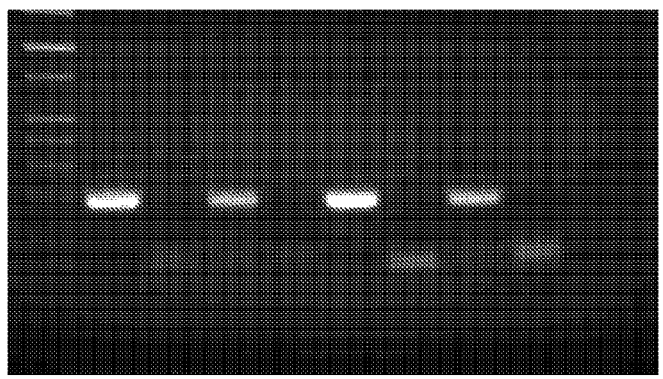
FIG. 6 illustrates that the RT-PCR product for the CCK-C receptor is found in 4 of 6 pancreatic cancer cell lines tested: BxPC-3, AsPC-1, MIAPaCa-2, and Panc-1. Levels of receptor were too low in SW1990 and Capan-1 cells to detect by end-point RT-PCR and may require more sensitive methods such as Real-Time or nested PCR.

Evaluation of CCK-C Receptor mRNA Expression in Human Pancreatic Cancer Cells and Clones by RT-PCR RNA was extracted according to the manufacturer's guidelines using a RNAeasy kit (qiagen, Valcenia). Total RNA (0.5 µg) underwent reverse transcription and PCR amplification by end-point RT-PCR using SSIII RT with Buffer C and Bio-X-Act short DNA polymerase (Bioline, Taunton, Mass.) and a two-steo RT-PCR kit (Invitrogen). Poly-A RNA was purified from some cancer cells lines for evaluation. The primers designed to amplify the PCR product for the CCK-C receptor spanned the $3_{rd}$ intron and included a downstream primer in the $4_{th}$ intron specific for the CCK-C receptor and not genomic DNA. PCR products were analyzed on an ethidium bromide stained gel with electrophoresis (FIG. 6).

Immunofluorescent Confocal Imaging of the CCK-C Receptor in Pancreatic Cancer Cells COS-1 cells were grown on cover slips in a 12-well dish at 1:10 dilution. Cells were grown for a day or two and then transiently transfected with PCDNA 3.1-CCKCR* I.2-I.3 using lipofectamine in a reduced serum media. Cells were allowed to grow for approximately 36 to 48 hours and immunocytochemistry was carried out.

Figure 7:
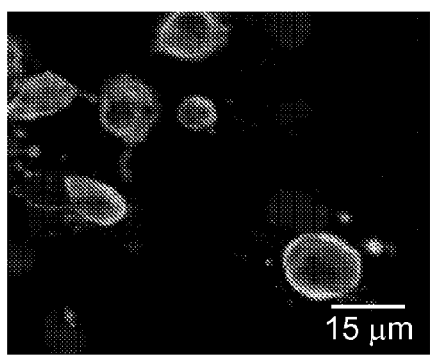
FIG. 7 is a confocal micrograph image of permeabilized CCK-C expressing cancer cells reacted with an Alexafluor-488 labeled CCK-C antibody showing the binding to the cytoplasmic membrane.

Cells were fixed with ice-cold methanol and acetone for 10 minutes each and rinsed with PBS. Permeabilization was done using 0.1% triton X100 in PBS and blocked with FBS (3 to 5%) for 1.5 hrs at room temperature. The cells were incubated with mouse monoclonal 3B93 1AB for the CCK-C receptor (1:200) at 40° C. O/N and washed with PBS and incubated with goat anti mouse-AF488 2AB (1:2000-1:5000) at room temperature for 1.5 hrs. Cells were then washed in PBS and coverslips mounted on to slides using DAPI mounting media. The cells were visualized and photographed using a Leica TCS SP2 AOBS confocal microscope using 63× objective at the appropriate laser settings (FIG. 7). Verified monoclonal antibodies were used to determine localization of the CCK-C receptor using confocal microscopy in permeabilized cancer cells (FIG. 7).

Electron Microscopy Localization of the CCK-C Receptor

Figure 8:
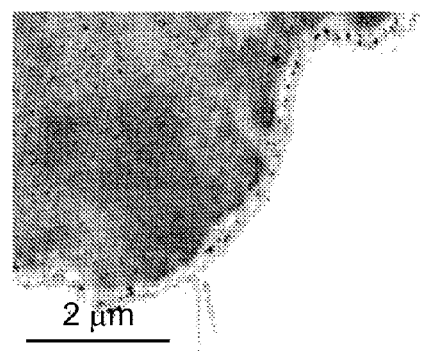
FIG. 8 is an EM image of the CCK-C monoclonal antibody in a CCK-C expressing pancreatic cancer cell with secondary gold labeling, shows the receptor location to intracytoplasmic membrane.

The cells were fixed with 4% formaldehyde in 0.1 M phosphate buffer PH 7.4 for approximately 1-1.5 hrs at 4° C. and rinsed W/ PBS. Permeabilization was done using 0.04% Saponin for 30 min, RT and rinsed W/PBS. Nonspecific sites were blocked using 5% FBS in PBS for 1.5 hrs, RT and rinsed W/PBS. 1AB incubation was done using mouse monoclonal 3B93 AB(1:200) in block buffer O/N at 4° C., washed with PBS and incubated with Nanogold-antimouse IgG (cat #2001, Nanoprobes) 2Ab (1:40) diluted in 5% FBS in PBS for 1.5 hrs at RT. Cells were washed with PBS and post fixed with 1.5% gluteraldehyde in PBS for 15 min, RT and rinsed with PBS. Silver enhancement was done using HQ Silver Enhancement Kit (cat #:2012) as per manufacturer's instructions for 4-8 minutes. The reaction was arrested by washing W/DH$_2$O, 5 min, several times. 0.2% Osmium treatment was done for 45 min on ice and rinsed with DH$_2$O, several times, 5 minutes each. The cells were counter stained with Uranyl acetate (0.25%) in 50% Ethanol for 20 to 30 min, room temperature and dehydrated in increasing concentrations of Ethanol (50%, 70%, 90%, 100%) each 3-5 minutes. Cells were then infiltrated with graded mixtures of Ethanol:Resin starting at 1:1 (O/N) followed by 4-5 changes of 100% resin, each 2-3 hrs. Finally the cover slips embedded W/100% resin in an aluminum dish and polymerized by drying in a 60° C. incubator for approximately 24 to 48 hours. Blocks were counter stained with either 2% uranyl acetate/lead citrate or both and ultra thin sections (80 nm) were done in the core EM lab and placed in copper grids. The sections were visualized and photographed in JEOL JEM 1400 DIGITAL Capture Transmission Electron Microscope (TEM) in the core EM facility (FIG. 8). Electron microscopy using the CCK-C receptor monoclonal antibody and secondary gold labeled antibody shows the antibody binds to an intracytoplasmic plasma membrane domain (FIG. 8). The intracellular binding location of the monoclonal antibody was confirmed by demonstrating no binding in nonpermeabilized cells.

CONCLUSION

Our laboratory was the first to characterize the role of CCK and gastrin on growth of human pancreatic cancer and to identify the receptor involved with CCK or gastrin-stimulated growth. We have discovered, cloned and sequenced a new receptor on pancreatic cancer cells that is not found in normal pancreas. This receptor is a splice variant of the CCK-B receptor and retains the mis-spliced 4th intron which encodes for an additional 69-amino acids. Using this portion of the novel receptor which distinguishes the CCK-C receptor from the normal CCK-B receptor, we have raised antibodies in chicken, rabbits, and mice. The receptor is a functionally significant receptor since removal of the receptor by antisense techniques or blockage with antibodies impairs cancer cell growth. Additionally, the CCK-C cancer receptor RNA is detected in pancreatic cancer cells and tissues by RT-PCR and immunohistochemistry. In our prior publication, we showed that growth of human pancreatic cancer is inhibited by the selective CCK-C antibody raised in chicken suggesting that this antibody may have potential therapeutic use in humans if a humanized antibody could be developed. Since the receptor is identified by immunofluorescence the antibody may possibly be used for early detection or staging of pancreatic cancer using fluorescent methods such as PET scanning or FAC sorting.

REFERENCE LIST

1. Rocha Lima, C. M. and Centeno, B. Update on pancreatic cancer. Curr. Opin. Oncol., 14: 424-430, 2002.
2. Jemal, A., Murray, T., Samuels, A., Ghafoor, A., Ward, E., and Thun, M. J. Cancer statistics, 2003. CA Cancer J. Clin., 53: 5-26, 2003.
3. Bramhall, S., Dunn, J. A., and Neoptolemos, J. P. Epidemiology of pancreatic cancer. In H. G. Beger, A. L. Warshaw, M. W. Buchler, D. L. Carr-Locke, J. P. Neoptolemos, C. Russel, and M. G. Sarr (eds.), The Pancreas, 1st ed, pp. 889-906. Massachusetts: Blackwell Science, Inc., 1998.
4. Heinemann, V. Gemcitabine-based combination treatment of pancreatic cancer. Semin. Oncol., 29: 25-35, 2002.
5. McGinn, C. J., Lawrence, T. S., and Zalupski, M. M. On the development of gemcitabine-based chemoradiotherapy regimens in pancreatic cancer. Cancer, 95: 933-940, 2002.
6. Oettle, H. and Riess, H. Gemcitabine in combination with 5-fluorouracil with or without folinic acid in the treatment of pancreatic cancer. Cancer, 95: 912-922, 2002.
7. Blackstock, A. W., Bernard, S. A., Richards, F., Eagle, K. S., Case, L. D., Poole, M. E., Savage, P. D., and Tepper, J. E. Phase I trial of twice-weekly gemcitabine and concurrent radiation in patients with advanced pancreatic cancer. J. Clin. Oncol., 17: 2208-2212, 1999.
8. Schally, A. V. and Nagy, A. Chemotherapy targeted to cancers through tumoral hormone receptors. Trends Endocrinol. Metab, 15: 300-310, 2004.
9. Slamon, D. J., Leyland-Jones, B., Shak, S., Fuchs, H., Paton, V., Bajamonde, A., Fleming, T., Eiermann, W., Wolter, J., Pegram, M., Baselga, J., and Norton, L. Use of chemotherapy plus a monoclonal antibody against HER2 for metastatic breast cancer that overexpresses HER2. N. Engl. J. Med., 344: 783-792, 2001.
10. Xiong, H. Q., Rosenberg, A., LoBuglio, A., Schmidt, W., Wolff, R. A., Deutsch, J., Needle, M., and Abbruzzese, J. L. Cetuximab, a monoclonal antibody targeting the epidermal growth factor receptor, in combination with gemcitabine for advanced pancreatic cancer: a multicenter phase II Trial. J. Clin. Oncol., 22: 2610-2616, 2004.
11. Hurwitz, H. Integrating the Anti-VEGF-A Humanized Monoclonal Antibody Bevacizumab with Chemotherapy in Advanced Colorectal Cancer. Clin. Colorectal Cancer, 4 *Suppl* 2: S62-S68, 2004.
12. Kindler, H., Ansari, R., Lester, E., Locker, G., Nattam, S., Stadler, W., Wade-Oliver, K., and Vokes, E. Bevacizumab (B) plus gemcitabine (G) in patients (pts) with advanced pancreatic cancer (PC). Proc Am Soc Clin Oncol, 22: 259, 2003.
13. Soll, A. H. and Berglindh T. Receptors that regulate gastric acid-secretory function. In L. R. Johnson (ed.), Physiology of the gastrointestinal tract, vol. 1, 3rd ed, pp. 1139-1170. New York: Raven Press, 1994.
14. Solomon, T. E. Control of exocrine pancreatic secretion. In L. R. Johnson (ed.), Physiology of the gastrointestinal tract, vol. 1, 3rd ed, pp. 1499-1530. New York: Raven Press, 1994.
15. Moran, T. H., Sawyer, T. K., Seeb, D. H., Ameglio, P. J., Lombard, M. A., and McHugh, P. R. Potent and sustained satiety actions of a cholecystokinin octapeptide analogue. Am. J. Clin. Nutr., 55: 286S-290S, 1992.

16. Dembinski, A. B. and Johnson, L. R. Stimulation of pancreatic growth by secretin, caerulein, and pentagastrin. Endocrinology, 106: 323-328, 1980.
17. Majumdar, A. P. and Johnson, L. R. Gastric mucosal cell proliferation during development in rats and effects of pentagastrin. Am. J. Physiol, 242: G135-G139, 1982.
18. Hakanson, R. and Sundler, F. Trophic effects of gastrin. Scand. J. Gastroenterol. Suppl, 180: 130-136, 1991.
19. Johnson, L. R. and McCormack, S. A. Regulation of gastrointestinal mucosal growth. In L. R. Johnson (ed.), Physiology of the gastrointestinal tract, vol. 1, 3rd ed, pp. 611-642. New York: Raven Press, 1994.
20. Singh, P., Walker, J. P., Townsend, C. M., Jr., and Thompson, J. C. Role of gastrin and gastrin receptors on the growth of a transplantable mouse colon carcinoma (MC-26) in BALB/c mice. Cancer Res., 46: 1612-1616, 1986.
21. Smith, J. P. and Solomon, T. E. Effects of gastrin, proglumide, and somatostatin on growth of human colon cancer. Gastroenterology, 95: 1541-1548, 1988.
22. Smith, J. P., Stock, E. A., Wotring, M. G., McLaughlin, P. J., and Zagon, I. S. Characterization of the CCK-B/gastrin-like receptor in human colon cancer. Am. J. Physiol., 271: R797-R805, 1996.
23. Upp, J. R., Jr., Singh, P., Townsend, C. M., Jr., and Thompson, J. C. Clinical significance of gastrin receptors in human colon cancers. Cancer Res., 49: 488-492, 1989.
24. Smith, J. P., Shih, A. H., Wotring, M. G., McLaughlin, P. J., and Zagon, I. S. Characterization of CCK-B/gastrin-like receptors in human gastric carcinoma. Int. J. Oncol., 12: 411-419, 1998.
25. Watson, S., Durrant, L., and Morris, D. Gastrin: growth enhancing effects on human gastric and colonic tumor cells. Br. J. Cancer, 59: 554-558, 1989.
26. Rehfeld, J. F., Bardram, L., and Hilsted, L. Gastrin in human bronchogenic carcinomas: constant expression but variable processing of progastrin. Cancer Res., 49: 2840-2843, 1989.
27. Smith, J. P., Kramer, S. T., and Solomon, T. E. CCK stimulates growth of six human pancreatic cancer cell lines in serum-free medium. Regul. Pept., 32: 341-349, 1991.
28. Smith, J. P., Solomon, T. E., Bagheri, S., and Kramer, S. Cholecystokinin stimulates growth of human pancreatic adenocarcinoma SW-1990. Dig. Dis. Sci., 35: 1377-1384, 1990.
29. Smith, J. P., Fantaskey, A. P., Liu, G., and Zagon, I. S. Identification of gastrin as a growth peptide in human pancreatic cancer. Am. J. Physiol., 268: R135-R141, 1995.
30. Andren-Sandberg, A., Dawiskiba, S., and Ihse, I. Studies of the effect of cerulein administration on experimental pancreatic carcinogenesis. Scand. J. Gastroenterol., 19: 122-128, 1984.
31. Howatson, A. G. and Carter, D. C. Pancreatic carcinogenesis-enhancement by cholecystokinin in the hamster-nitrosamine model. Br. J. Cancer, 51: 107-114, 1985.
32. Brand, S. J. and Fuller, P. J. Differential gastrin gene expression in rat gastrointestinal tract and pancreas during neonatal development. J. Biol. Chem., 263: 5341-5347, 1988.
33. Smith, J. P., Shih, A., Wu, Y., McLaughlin, P. J., and Zagon, I. S. Gastrin regulates growth of human pancreatic cancer in a tonic and autocrine fashion. Am. J. Physiol., 270: R1078-R1084, 1996.
34. Pisegna, J. R., de Weerth, A., Huppi, K., and Wank, S. A. Molecular cloning of the human brain and gastric cholecystokinin receptor: structure, functional expression and chromosomal localization. Biochem. Biophys. Res. Commun., 189: 296-303, 1992.
35. Wank, S. A., Harkins, R., Jensen, R. T., Shapira, H., de Weerth, A., and Slattery, T. Purification, molecular cloning, and functional expression of the cholecystokinin receptor from rat pancreas. Proc. Natl. Acad. Sci. U.S.A, 89: 3125-3129, 1992.
36. Wank, S. A., Pisegna, J. R., and de Weerth, A. Brain and gastrointestinal cholecystokinin receptor family: structure and functional expression. Proc. Natl. Acad. Sci. U.S.A, 89: 8691-8695, 1992.
37. Wank, S. A. G protein-coupled receptors in gastrointestinal physiology. I. CCK receptors: an exemplary family. Am. J. Physiol, 274: G607-G613, 1998.
38. Smith, J. P., Verderame, M. F., McLaughlin, P., Martenis, M., Ballard, E., and Zagon, I. S. Characterization of the CCK-C (cancer) receptor in human pancreatic cancer. Int. J. Mol. Med., 10: 689-694, 2002.
39. Smith, J. P., Rickabaugh, C. A., McLaughlin, P. J., and Zagon, I. S. Cholecystokinin receptors and PANC-1 human pancreatic cancer cells. Am. J. Physiol, 265: G149-G155, 1993.
40. Smith, J. P., Liu, G., Soundararajan, V., McLaughlin, P. J., and Zagon, I. S. Identification and characterization of CCK-B/gastrin receptors in human pancreatic cancer cell lines. Am. J. Physiol, 266: R277-R283, 1994.
41. Smith, J. P. and Zagon, I. S. Cholecystokinin receptors and human pancreatic adenocarcinomas. Int J Pancreatology, 16: 243-246, 1994.
42. Smith, J. P., Kramer, S. T., and Cheung, J. Y. Effects of cholecystokinin on cytosolic calcium in human pancreatic cancer cells. Regul. Pept., 36: 299-310, 1991.
43. Smith, J. P., Verderame, M. F., McLaughlin, P., and Zagon, I. S. Characterization of the CCK-C (cancer) receptor in human pancreatic cancer. Digestion 60, 401. 1999.
Ref Type: Abstract
44. Biagini, P., Monges, G., Vuaroqueaux, V., Parriaux, D., Cantaloube, J. F., and De Micco, P. The human gastrin/cholecystokinin receptors: type B and type C expression in colonic tumors and cell lines. Life Sci., 61: 1009-1018, 1997.
45. Song, I., Brown, D. R., Wiltshire, R. N., Gantz, I., Trent, J. M., and Yamada, T. The human gastrin/cholecystokinin type B receptor gene: alternative splice donor site in exon 4 generates two variant mRNAs. Proc. Natl. Acad. Sci. U.S.A, 90: 9085-9089, 1993.
46. Hellmich, M. R., Rui, X. L., Hellmich, H. L., Fleming, R. Y., Evers, B. M., and Townsend, C. M., Jr. Human colorectal cancers express a constitutively active cholecystokinin-B/gastrin receptor that stimulates cell growth. J Biol. Chem., 275: 32122-32128, 2000.
47. Ding, W. Q., Kuntz, S. M., and Miller, L. J. A misspliced form of the cholecystokinin-B/gastrin receptor in pancreatic carcinoma: role of reduced sellular U2AF35 and a suboptimal 3'-splicing site leading to retention of the fourth intron. Cancer Res., 62: 947-952, 2002.
48. Smith, J. P., Verderame, M. F., Ballard, E. N., and Zagon, I. S. Functional significance of gastrin gene expression in human cancer cells. Regul. Pept., 117: 167-173, 2004.
49. Smith, J. P., Stanley, W. B., Verderame, M. F., and Zagon, I. S. Functional significance of the CCK-C receptor in human pancreatic cancer. Pancreas, 29: 271-277, 2004.
50. Smith, J. P., Hamory, M. W., Verderame, M. F., and Zagon, I. S. Quantitative analysis of gastrin mRNA and peptide in normal and cancerous human pancreas. Int. J. Mol. Med., 2: 309-315, 1998.
51. Kaufmann, R., Schafberg, H., Rudroff, C., Henklein, P., and Nowak, G. Cholecystokinin B-type receptor signaling is involved in human pancreatic cancer cell growth. Neuropeptides, 31: 573-583, 1997.
52. Smith, J. P., Verderame, M. F., McLaughlin, P. J., and Zagon, I. S. Characterization of the CCK-C (cancer) receptor in human pancreatic cancer. Gastroenterology, 116: A1164, 1999

I claim:

1. A method for treating a patient with a gastrointestinal or other tumor which possess the CCK-C receptor comprising administering to the patient a therapeutically effective dose of the 3B9.1 monoclonal antibody to the CCK-C receptor wherein binding of the antibody interferes with the growth of the cancerous material.

2. The method of claim 1 in which the antibody may be combined with other agents or administered by nanotechnology including nanoparticles and nanoliposomes or other vehicle carrier devised to improve the target specific binding for staging and therapy.

* * * * *